US 8,398,932 B2

(12) United States Patent
Busujima

(10) Patent No.: US 8,398,932 B2
(45) Date of Patent: Mar. 19, 2013

(54) CULTURE APPARATUS

(75) Inventor: Hiroki Busujima, Ota (JP)

(73) Assignee: Panasonic Healthcare Co., Ltd., Toon-shi, Ehime (JP)

(*) Notice: Subject to any disclaimer, the term of this patent is extended or adjusted under 35 U.S.C. 154(b) by 848 days.

(21) Appl. No.: 12/294,157

(22) PCT Filed: Mar. 8, 2007

(86) PCT No.: PCT/JP2007/054535
§ 371 (c)(1),
(2), (4) Date: Feb. 12, 2009

(87) PCT Pub. No.: WO2007/111105
PCT Pub. Date: Oct. 4, 2007

(65) Prior Publication Data
US 2009/0227008 A1  Sep. 10, 2009

(30) Foreign Application Priority Data

Mar. 27, 2006 (JP) ................... 2006-85892

(51) Int. Cl.
*A61L 2/00* (2006.01)
*A61L 9/00* (2006.01)
*C12M 1/34* (2006.01)
*G01N 21/00* (2006.01)
*A24F 25/00* (2006.01)

(52) U.S. Cl. ........ 422/305; 422/292; 422/300; 422/302; 422/304; 422/306; 422/308; 435/287.1; 435/289.1; 250/454.11; 250/455.11; 250/492.1; 239/34; 239/44

(58) Field of Classification Search .................. 422/292, 422/300, 302, 304, 306, 308, 305; 435/287.1, 435/289.1; 250/454.11, 455.11, 492.1; 239/34, 239/44
See application file for complete search history.

(56) References Cited

U.S. PATENT DOCUMENTS 3,958,935 A  5/1976 Kowol ............................ 21/58
5,091,107 A  2/1992 Hutchings ................ 252/187.21
(Continued)

FOREIGN PATENT DOCUMENTS
JP  61-025688 A  2/1986
JP  62-060556 A  3/1987
(Continued)

OTHER PUBLICATIONS

Office Action dated Oct. 18, 2011 issued in corresponding Japanese Patent Application No. 2006-85892.
Yonehiro Kanamura et at, "Heisagata Hito Saibo Baiyo System (AIST) o Mochiita Hito Saito no Baiyo Hinshitsu kanri Gijutsu no Kaihatsu", PDA Journal of GFMP and Validation in Japan, 2005, vol. 7, No. 2, pp. 135 to 145.

(Continued)

*Primary Examiner* — Jill Warden
*Assistant Examiner* — Monzer Chorbaji
(74) *Attorney, Agent, or Firm* — Kratz, Quintos & Hanson, LLP

(57) ABSTRACT

A culture apparatus which is capable of shortening sterilization time includes a gas concentration measuring sensor, pipes connected to a gas concentration measuring device and every corner of a cultivating chamber, and a sterilizing gas generator that supplies sterilizing gas into a cultivating chamber and atomizes a sterilizer solution (oxygenated water) by means of an ultrasonic vibrator. The culture apparatus further includes an ultraviolet lamp that irradiates gas in the cultivating chamber, a freely opening/closing door, a door-locking device, and a controller for controlling the locking device to prevent the door from being opened from start of the sterilization process to end of the decomposition process.

18 Claims, 2 Drawing Sheets

U.S. PATENT DOCUMENTS

| | | | |
|---|---|---|---|
| 6,593,131 B2 | 7/2003 | Tamaoki et al. | 435/286.1 |
| 6,767,509 B1 * | 7/2004 | Griesbach et al. | 422/29 |
| 2003/0012689 A1 * | 1/2003 | Caputo et al. | 422/32 |
| 2004/0005240 A1 | 1/2004 | Adiga et al. | 422/1 |
| 2005/0170491 A1 * | 8/2005 | Takagi et al. | 435/287.1 |
| 2005/0220665 A1 | 10/2005 | Ding | 422/20 |

FOREIGN PATENT DOCUMENTS

| | | |
|---|---|---|
| JP | 09-060931 A | 3/1997 |
| JP | 10-057465 A | 3/1998 |
| JP | 2000-166536 A | 6/2000 |
| JP | 2001-518816 A | 10/2001 |
| JP | 2005-237774 A | 9/2005 |
| JP | 2005-278566 A | 10/2005 |
| WO | WO 2004/011593 A1 | 2/2004 |
| WO | WO 2006/016620 | 2/2006 |

OTHER PUBLICATIONS

Koei Ko et al, Kasankasuiso to Sono Kankyo Hozen eno Oyo, Journal of water and waste 1997, vol. 39, No. 7, pp. 565-570.

PCT Notification of Transmittal of translation of the International Preliminary Report on Patentability (PCT Chapter I) dated Oct. 21, 2008.

European Search Report issued in corresponding application mailed Jul. 6, 2012 (4 pages).

Database WPI Week 200616, Thomson Scientific, London, GB, AN 2006-155943 XP002678737 & WO 2006/016620 (Bio Media Co. Ltd.), Feb. 16, 2006 Abstract.

* cited by examiner

CULTURE APPARATUS

BACKGROUND OF THE INVENTION

This invention relates to a culture apparatus for cultivating (or incubating) cultures such as cells, microbes and the like in a cultivating chamber.

A culture apparatus, which has been conventionally called an incubator, cultivates cultures (samples) such as cells, microbes and the like as culture targets in an aseptic cultivating chamber while keeping temperature of the cultivating chamber and gas concentration of carbon dioxide ($CO_2$), Oxygen ($O_2$) or the like constant. As shown in FIG. 4, a culture apparatus 100 includes an insulating box body 102 comprising an outer metal box 110 having an opening 102A at one side thereof and an inner stainless box 116 provided inside the outer box 110. In addition, a cultivating chamber 104 is formed in a space (inner box 116) surrounded by a door (inner door 118) blocking the opening 102A in a free-opening/closing manner. The cultivating chamber 104 is vertically partitioned by a plurality of shelves 106 on which vessels 108 that contain cultures are placed.

The culture apparatus 100 is provided with an air circulation fan 128 for controlling circumferences in the cultivating chamber 104, which is arranged in a duct 124, and a gas concentration measuring device 130 having a gas concentration measuring sensor for carbon dioxide or oxygen (not shown). The gas concentration measuring device 130 communicates to the cultivating chamber 104 via pipes 134 and 136 for guiding gas in the cultivating chamber 104 to the gas concentration measuring sensor. An ultraviolet lamp 150, which is arranged within the cultivating chamber 104, irradiates the cultivating chamber 104 with an ultraviolet ray to sterilize circulating air, and gas is gathered from a measuring hole 138 stopped by a rubber stopper 140 for the purpose of measuring gas concentration in the cultivating chamber 104.

The insulating box body 102 is provided with an outer door 114 for blocking the opening 102A in a free-opening/closing manner, and the cultures are sent in and drawn out of the cultivating chamber 104 by opening/closing of the outer door 114 and the inner door 118. An insulating material 112 for heat conservation is provided inside the outer box 110, and a circulation path 120 of air or water is formed between the inner box 116 and the outer box 110. A heater 122 is arranged in the circulation path 120. Heat generated from the heater 122 is transferred to the cultivating chamber 104 by thermal conduction to the inner box 116 and heat transfer from the circulation path 120 by air or water to keep the cultivating chamber 104 at a temperature appropriate for cultivation. This allows the cultures, such as cells, microbes and the like, to be cultivated in the cultivating chamber 104 (see Japanese Patent Application Publication No. 2005-118021).

Such a culture apparatus 100 should be used while keeping the cultivating chamber 104 clean at all times. However, if cultivated cells or microbes are infected with bacteria, virus or the like, the cultivating chamber 104 and air in the cultivating chamber 104 of the culture apparatus are contaminated. Thus, in order to keep the cultivating chamber 104 clean, the cultivating chamber 104 is swept clean or is sterilized by being heated at a high temperature of more than 90° C. with a heater (not shown).

As described above, in the prior art, in order to keep the cultivating chamber clean, the cultivating chamber 104 has to be swept clean or be sterilized by being heated at a high temperature of more than 90° C. with a heater. However, this technique could not thoroughly sterilize the culture apparatus including the gas concentration measuring sensor, the pipes connected to the gas concentration measuring device and every corner of the cultivating chamber.

In addition, heat-resistant germs are incompletely sterilize even at the high temperature of more than 90° C., and further, about 8 hours are required to restart the cultivation through a cooling process from the increase of temperature of the cultivating chamber for sterilization by heating. This may lead to a problem of too much time during which the culture apparatus can not be used for cultivation.

SUMMARY OF THE INVENTION

The present invention has made to overcome such a problem and it is an object of the invention to provide a culture apparatus which is capable of shortening a sterilization time and sterilizing the culture apparatus including a gas concentration measuring sensor, pipes connected to a gas concentration measuring device and every corner of a cultivating chamber.

According to a first aspect of the invention, there is provided a culture apparatus for cultivating cultures such as cells, microbes or the like in a cultivating chamber, including a sterilizing gas generator that supplies sterilizing gas into the cultivating chamber.

According to a second aspect of the invention, in the first aspect, the sterilizing gas generator atomizes a sterilizer solution by means of an ultrasonic vibrator.

According to a third aspect of the invention, in the first aspect, the sterilizing gas generator evaporates a sterilizer solution by dipping an absorbing member into the sterilizer solution.

According to a fourth aspect of the invention, in one of the first to third aspects, the sterilizing gas concentration in the cultivating chamber is from 0.1 ppm to 100 ppm.

According to a fifth aspect of the invention, in one of the first to fourth aspects, the culture apparatus further includes an ultraviolet generator that irradiates gas in the cultivating chamber with an ultraviolet ray.

According to a sixth aspect of the invention, in the fifth aspect, the culture apparatus further includes a controller that performs a sterilization process for filling the cultivating chamber with the sterilizing gas for a predetermined period of time and a decomposition process for decomposing the sterilizing gas by irradiating the gas in the cultivating chamber with the ultraviolet ray by means of the ultraviolet generator.

According to a seventh aspect of the invention, in the sixth aspect, the culture apparatus further includes a door for blocking an opening of the cultivating chamber in a free-opening/closing manner and a locking device for prohibiting the door from being opened, and the controller controls the locking device to prevent the door from being opened from start of the sterilization process to end of the decomposition process.

According to the first aspect of the invention, since the culture apparatus for cultivating cultures such as cells, microbes or the like in the cultivating chamber, includes the sterilizing gas generator that supplies sterilizing gas into the cultivating chamber, it is possible to eradicate sundry germs inside the apparatus including the cultivating chamber before or after the cultivation operation. Accordingly, it is possible to realize a smooth cultivation operation in the cultivating chamber.

According to the second aspect of the invention, in the first aspect, since the sterilizing gas generator atomizes the sterilizer solution by means of the ultrasonic vibrator, it is possible to atomize a sundry germs sterilizer and fill the cultivating chamber with the atomized sterilizer as a gas without decomposing the sterilizer, unlike a heat and atomization method. Accordingly, it is possible to efficiently sterilize the inside of the apparatus.

According to the third aspect of the invention, in the first aspect, since the sterilizing gas generator evaporates the sterilizer solution by dipping the absorbing member into the sterilizer solution, it is possible to effectively generate the sterilizing gas to sterilize the inside of the apparatus while simplifying the configuration of the apparatus.

According to the fourth aspect of the invention, in one of the first to third aspects, since the sterilizing gas concentration in the cultivating chamber is from 0.1 ppm to 100 ppm, it is possible to reliably sterilize the inside of the apparatus.

According to the fifth aspect of the invention, in one of the first to fourth aspects, since the culture apparatus further includes the ultraviolet generator that irradiates gas in the cultivating chamber with the ultraviolet ray, it is possible to quickly lower the concentration of the sterilizing gas to a concentration harmless to a human body after sterilizing the inside of the apparatus with the sterilizing gas. Accordingly, it is possible to reduce wait time until the next cultivation operation starts.

According to the sixth aspect of the invention, in the fifth aspect, since the culture apparatus further includes the controller that performs the sterilization process for filling the cultivating chamber with the sterilizing gas for the predetermined period of time and the decomposition process for decomposing the sterilizing gas by irradiating the gas in the cultivating chamber with the ultraviolet ray by means of the ultraviolet generator, it is possible to automate operation from the sterilization of the inside of the apparatus with the sterilizing gas to the decomposition of the sterilizing gas, thereby remarkably improving workability.

According to the seventh aspect of the invention, in the sixth aspect, since the culture apparatus further includes the door for blocking the opening of the cultivating chamber in the free-opening/closing manner and the locking device for prohibiting the door from being opened, and the controller controls the locking device to prevent the door from being opened from start of the sterilization process to end of the decomposition process, it is possible to prevent the door from being opened by mistake before the sterilizing gas concentration is lowered to a valve harmless to a human body by the ultraviolet ray after the inside of the apparatus is sterilized with the sterilizing gas, thereby securing safety of the apparatus.

DETAILED DESCRIPTION OF THE PREFERRED EMBODIMENT

The most important feature of the present invention is to sterilize every corner of a cultivating chamber thoroughly and shorten time taken from sterilizing start to sterilizing end for the cultivating chamber. The purpose of sterilizing every corner of the cultivating chamber thoroughly and shortening time taken from the sterilizing start to the sterilizing end for the cultivating chamber can be accomplished by a simple configuration that a sterilizing gas generator is merely provided within the cultivating chamber.

Embodiment 1

Figure 1:
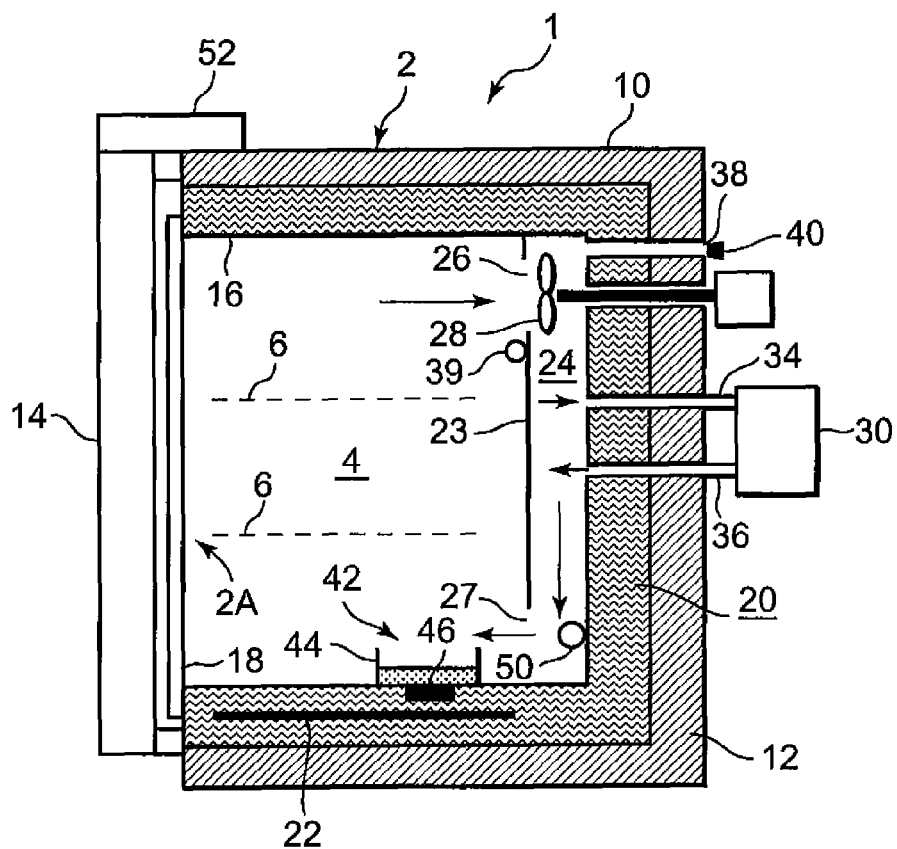
FIG. 1 is an end side view showing a structure of a culture apparatus according to an embodiment (Embodiment 1) of the present invention.
Figure 2:
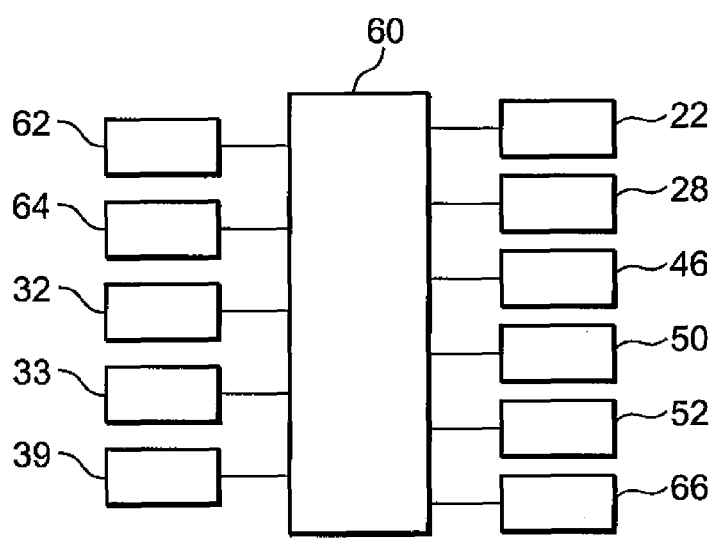
FIG. 2 is a block diagram of a control circuit for controlling the culture apparatus of the present invention.

Hereinafter, embodiments of the present invention will be described with reference to the drawings. FIG. 1 is an end side view showing a structure of a culture apparatus 1 according to an embodiment of the present invention, and FIG. 2 is a block diagram of a control circuit for controlling the culture apparatus 1 of the present invention.

In this embodiment, as shown in FIG. 1, the culture apparatus 1 includes an insulating box body 2 comprising an outer metal box 10 having an opening 2A at one side thereof and an inner stainless box 16. In addition, the opening 2A of the inner box 16 is provided with a transparent inner door 18 whose right side is supported to the insulating box body 2 by a hinge in a free-opening/closing manner. The inner door 18 blocks the opening 2A air-tightly by means of a gasket (not shown) provided in the opening 2A of the insulating box body 2.

A cultivating chamber 4 is formed in a space (inner box 16) surrounded by an inner door 18 blocking the opening 2A in a free-opening/closing manner. Within the cultivating chamber 4A are provided a plurality (2 in this embodiment) of shelves 6 that vertically partitions the cultivating chamber 4. Cultures received in the cultivating chamber 4 are sent in and drawn out of the cultivating chamber 4 by opening/closing of an outer door 14 and the inner door 18. In addition, vessels (not shown) that contain the cultures are placed on the shelves 6.

An insulating material 12 for heat conservation is provided inside the outer box 10, and a circulation path 20 of air or water is formed between the inner box 16 and the outer box 10. A heater 22 is arranged in the circulation path 20 (in the lower side of the cultivating chamber 4). When the heater 22 is heated, heat generated from the heater 22 is transferred to the cultivating chamber 4 by thermal conduction to the inner box 16 and heat transfer from the circulation path 20 by air or water to keep the cultivating chamber 4 at a temperature appropriate for cultivation.

In addition, a rear wall 23 is provided in the rear side of the cultivating chamber 4 and a duct 24 is provided between the rear wall 23 and the inner box 16. An inlet 26 communicating to the cultivating chamber 4 is provided in the upper side of the duct 24 and an outlet 27 is provided in the lower side of the duct 24. In addition, an air circulation fan 28 for controlling circumferences in the cultivating chamber 4 is arranged inside the duct 24 at a position corresponding to the inlet 26. Air in the cultivation chamber 4 is absorbed through the inlet 26 into the duct 24 by means of the fan 28, and the absorbed air is discharged through the outlet 27 at the lower side of the duct 24 into the cultivating chamber 4 (as indicated by arrows in FIG. 1). Such a configuration allows the air to be forcedly circulated in the cultivating chamber 4.

In addition, the culture apparatus 1 is provided with a gas concentration measuring device 30 having a gas concentration measuring sensor 32 (shown in FIG. 2) therein to measure the concentration of carbon dioxide ($CO_2$) or oxygen ($O_2$) supplied into the cultivating chamber 4, and an oxygenated water measuring sensor 39 to measure oxygenated water gas in the cultivating chamber 4. The gas concentration measuring device 30 communicates to the cultivating chamber 4 via two pipes 34 and 36 to guide gas in the cultivating chamber 4 (and in the duct 24) to the gas concentration measuring sensor 32. In addition, a fan 33 (shown in FIG. 2) for absorbing the gas in the cultivating chamber 4 into the gas concentration measuring device 30 to measure gas concentration and then returning the gas to the duct 24 is connected to the gas concentration measuring device 30.

In more detail, the gas concentration measuring sensor 32 is configured to detect the gas concentration in the cultivating chamber 4 by absorbing the gas in the duct 24 (in the cultivating chamber 4) via one pipe 34 and discharging the absorbed gas into the duct 24 via the other pipe 36. In addition, the culture apparatus 1 is provided with a measuring hole 38 stopped by a rubber stopper 40 in order to measure the gas concentration in the cultivating chamber 4. When the rubber stopper 40 of the measuring hole 38 is unplugged by an operator, the concentration and components of the gas in the cultivating chamber 4 can be examined.

The culture apparatus 1 is connected by a pipe with a carbon dioxide supply device, an oxygen supply device (not shown) or the like to supply cultivation gas such as carbon dioxide or oxygen gas into the cultivating chamber 4. In addition, inside the cultivating chamber 4 is provided a sterilizing gas generator 42 to atomize oxygenated water (corresponding to a sterilizer solution in the present invention).

For example, the sterilizing gas generator 42 generates gas by atomizing the oxygenated water as the sterilizer solution in the cultivating chamber 4 by means of an ultrasonic wave. The sterilizing gas generator 42 includes a stainless vessel 44 (typically called a butt) provided in the bottom of the inner box 16 and an ultrasonic vibrator 46. In addition, an electronic valve 66 (shown in FIG. 2) to control the amount of supply of carbon dioxide gas, oxygen gas and sterilizing gas by its opening/closing is provided the pipe connected to the carbon dioxide supply device or the oxygen supply device.

The vessel 44 has its top side opened, has a size as large as to accommodate the predetermined amount of oxygenated water, and is provided near the front (in the cultivating chamber 4) of the outlet 27 of the duct 24. In addition, the bottom of the vessel 44 is depressed into the circulation path 20 by a predetermined dimension and the ultrasonic vibrator 46 is provided within the depressed vessel 44. Hydrogen peroxide gas (corresponding to the sterilizing gas in the present invention) as a sterilizer is supplied by a predetermined amount by an operator. When the oxygenated water is evaporated by a heating type humidifier which is currently frequently being used, since hydrogen peroxide (sterilizer) is decomposed, the ultrasonic vibrator 46 is attached to an outer side (in the circulation path 20) of the bottom of the cultivating chamber 4 in the present invention. The ultrasonic vibrator 46 can atomize the hydrogen peroxide without heating it. Since a technique for the ultrasonic vibrator 46 to atomize the hydrogen peroxide at a low temperature is well known in the art, explanation of which will be omitted.

An ultraviolet lamp 50 (corresponding to an ultraviolet generator in the present invention) for generating an ultraviolet ray is arranged in the culture apparatus 1. The ultraviolet ray emitted from the ultraviolet lamp 50 decomposes the sterilizing gas circulating in the duct 24, thereby making it harmless. To make the sterilizing gas harmless by the ultraviolet lamp 50 will be described in detail later.

When the oxygenated water is atomized and gasified by the ultrasonic wave to sterilize the cultivating chamber 4 in the culture apparatus 1, if the outer door 14 is carelessly opened, the sterilizing gas is get out of the cultivating chamber 4, which may result in danger to a human body. So, in the present invention, the culture apparatus 1 includes a locking device 52 to prevent the outer door from being released while the cultivating chamber 4 is sterilized with the oxygenated water. The locking device 52 is provided in the top side of the insulating box body 2 and between the outer box 10 and the outer door 14. The locking device 52 is fixed to the outer box 10, and in this state, the outer door 14 is configured to be openable/closable and the outer door 14 is configured to be locked/unlocked with the locking device 52.

In the meantime, as shown in FIG. 2, the culture apparatus 1 is provided with a controller 60. The controller 60 is, for example, a general-purpose microcomputer including a storing unit (memory) in which various data can be stored, a timer, etc. The controller 60 is connected with an operation switch 62 such as a power switch or a sterilization start switch (not shown), the gas concentration measuring sensor 32 provided in the gas concentration measuring device 30, a temperature sensor 64 for detecting the internal temperature of the cultivating chamber 4, an oxygenated water measuring sensor 39, etc.

In addition, the controller 60 is connected with a plurality of electronic valves 66 provided in pipes of the carbon dioxide gas supply device or the oxygen gas supply device, the ultraviolet lamp 50 for sterilization of circulation air, the air circulation fan 28 for controlling the circumferences in the cultivating chamber 4, etc. In addition, the controller 60 is connected with the heater 22 for heating the cultivating chamber 4 at a temperature appropriate for cultivation, the ultrasonic vibrator 46 for atomizing the oxygenated water, the locking device 52 for preventing the outer door 14 from being released.

The controller 60 has programs for a sterilization process for sterilizing the cultivation chamber 4 and a decomposition process for decomposing the sterilizing gas in the cultivating chamber 4 with the ultraviolet lamp 50 after the sterilization process, which are stored in the memory of the microcomputer.

Next, with the above configuration, the operation of the culture apparatus 1 will be described. In particular, in this embodiment, the sterilization process and the decomposition process of the culture apparatus 1 will be described. In the sterilization process of the culture apparatus 1, first, when the operation switch 62 (the sterilization start switch) is pushed by an operator, the controller 60 drives the locking device 52 to lock the outer door 14 and drives the fan 28. Accordingly, the air in the cultivating chamber 4 is absorbed into the duct 24 through the inlet 26 and is discharged into the cultivating chamber 4 from the bottom of the duct 24, circulating in the cultivating chamber 4 (see arrows indicated in FIG. 1).

The controller 60 opens the electronic valves 66 provided in the pipes and operates the fan 33. In addition, the controller 60 heats the heater, detects the temperature of the cultivating chamber 4 by means of the temperature sensor 64, and keeps the cultivating chamber 4 at a predetermined temperature (cultivation temperature in this case). Moreover, the controller 60 automatically interrupts the heat from the heater 22 after the decomposition process.

Next, the controller 60 drives the ultrasonic vibrator 46 with a preset timer for a predetermined period of time to atomize the oxygenated water in the vessel 44 and scatter the atomized oxygenated water into the cultivating chamber 4. As the cultivating chamber 4 is heated with the heater 22 at the predetermined temperature, the oxygenated water atomized and scattered into the cultivating chamber 4 is evaporated in a short time to be hydrogen peroxide gas with which the cultivating chamber 4 is filled. At this time, since the vessel 44 is filled with a predetermined amount of oxygenated water, the cultivating chamber 4 has hydrogen peroxide gas concentration of from 0.1 ppm to 100 ppm. The amount of oxygenated water in the vessel 44 is beforehand obtained by experiment such that the hydrogen peroxide gas concentration in the cultivating chamber 4 is from 0.1 to 100 ppm.

While the cultivating chamber 4 is sterilized with the hydrogen peroxide gas circulating by the fan 28, the gas in the duct 24 is absorbed into the gas concentration measuring device 30 through the pipe 34 by the fan 33 and then is returned to the duct 24 through the pipe 36. Accordingly, every corner of the cultivating chamber 4, the gas concentration measuring device 30 and the pipes 34 and 36, that is, all the inside of the culture apparatus 1 including the cultivating chamber 4, can be sterilized with efficiency.

In addition, since the oxygenated water supplied and stored in the vessel 44 is atomized and then evaporated, the inside of the culture apparatus 1 can be reliably sterilized with efficiency. In addition, since the ultrasonic vibrator 46 to atomize the oxygenated water does not heat and evaporate the oxygenated water, it is possible to atomize oxygenated water without decomposing a sundry germs sterilizer, unlike the heat and atomization.

After performing the sterilization process for a predetermined period of time, the controller 60 stops the ultrasonic vibrator 46 and turns on the ultraviolet lamp 50 provided in the duct 24 for transfer to the decomposition process. The controller 60 performs the sterilization process and the decomposition process in an automatic sequential manner. In the decomposition process, since the controller 60 operates the fans 28 and 33 and so on and turns on the ultraviolet lamp 50, the hydrogen peroxide gas inside the culture apparatus 1 is circulated to the ultraviolet lamp 50 and is decomposed by irradiation of the ultraviolet lamp 50. According to a decomposition reaction of the hydrogen peroxide, $H_2O_2 \rightarrow OH$ radicals $\rightarrow H_2O$, the hydrogen peroxide finally turns to harmless water.

The controller 60 continues to perform the decomposition process for the hydrogen peroxide gas by the ultraviolet ray from the ultraviolet lamp 50 until the concentration of the hydrogen peroxide gas in the cultivating chamber 4, which is detected by the oxygenated water measuring sensor 39, is lowered to a secure value to a human body. Accordingly, since the concentration of the hydrogen peroxide gas in the culture apparatus 1 can be quickly lowered to a value harmless to a human body, it is possible to significantly reduce wait time until the next cultivation operation starts.

When the decomposition process is completed, the controller 60 drives the locking device 52 to release the lock of the outer door 14. In this case, as the hydrogen peroxide gas (sterilizing gas) in the cultivating chamber 4 is forcedly decomposed with the ultraviolet ray, it is possible to significantly shorten the wait time till the next cultivation operation. Accordingly, it is possible to eradicate sundry germs inside the apparatus including the cultivating chamber 4 before or after the cultivation operation, thereby realizing a smooth cultivation operation in the cultivating chamber 4.

In addition, until the decomposition process is ended from the sterilization process in the culture apparatus 1, the controller 60 prohibits the outer door 14 from being opened by means of the locking device 52. Accordingly, it is possible to prevent the outer door 14 from being opened by mistake before the sterilizing gas concentration is lowered to a value harmless to a human body by the ultraviolet ray after the inside of the culture apparatus 1 is sterilized with the sterilizing gas. Thus, when the cultivating chamber 4 is sterilized with the sterilizing gas, it is possible to secure substantial safety of the culture apparatus 1.

Embodiment 2

Figure 3:
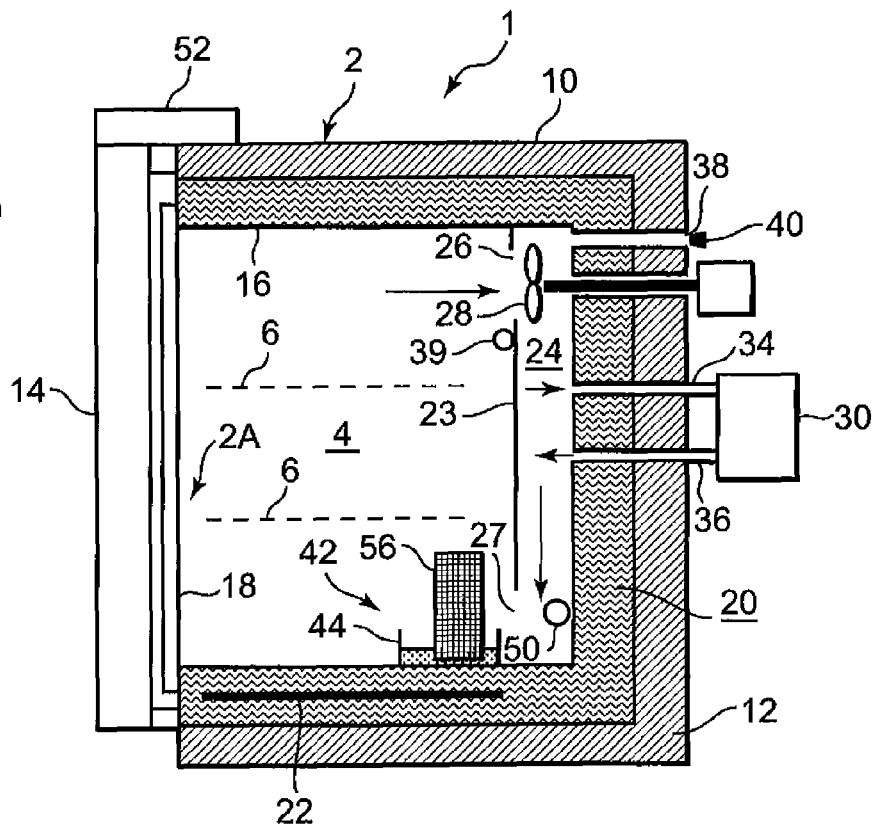
FIG. 3 is an end side view showing a structure of a culture apparatus according to another embodiment (Embodiment 2) of the present invention.
Figure 4:
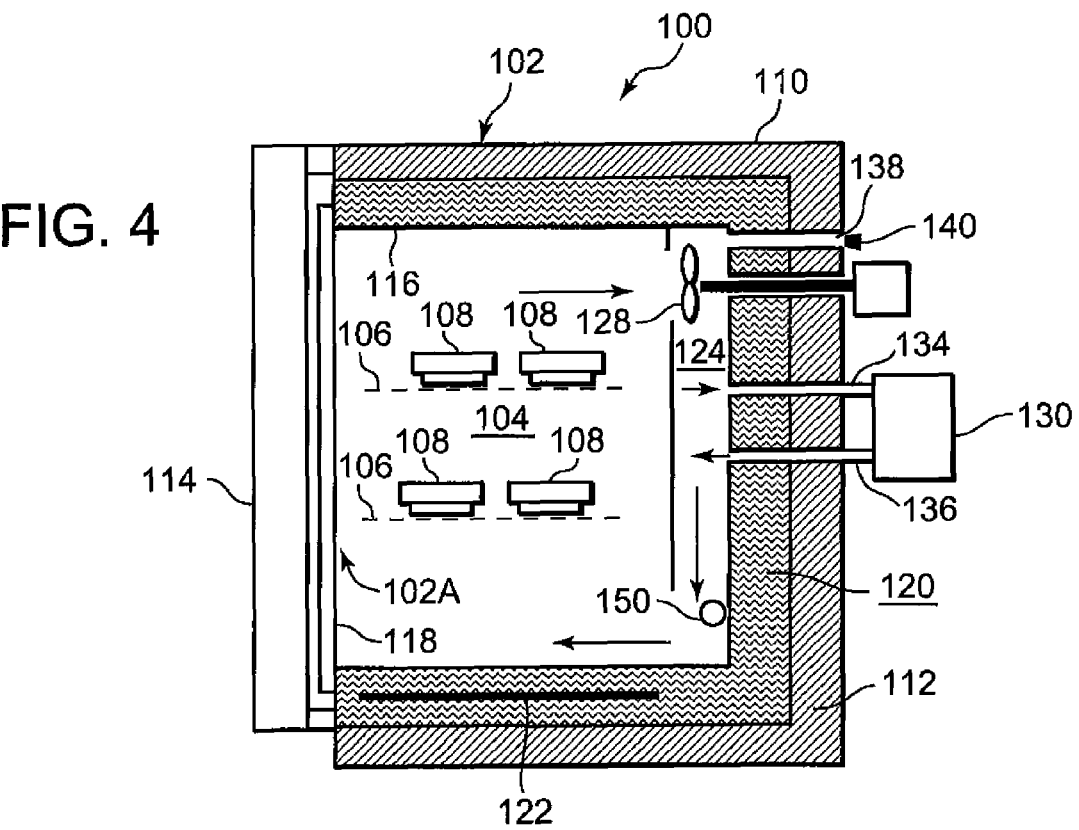
FIG. 4 is an end side view showing a structure of a conventional culture apparatus.

Next, FIG. 3 shows a culture apparatus 1 according to another embodiment of the present invention. The culture apparatus 1 of this embodiment has substantially the same configuration as the above-described embodiment. Hereinafter, only portions different from the above-described embodiment will be described. In the figure, the same elements as the above-described embodiment are denoted by the same reference numerals, and explanation of which will be omitted. As shown in FIG. 3, in the culture apparatus 1, the ultrasonic vibrator 46 of the sterilizing gas generator 42 in Embodiment 1 is replaced with an absorbing member 56. When the absorbing member 56 is dipped into oxygenated water, the oxygenated water is evaporated.

That is, the sterilizing gas generator 42 is provided with the absorbing member 56 erecting in the vessel 44 having flat bottom. A frame (not shown) made of stainless steel or synthetic resin is provided around the absorbing member 56. A given wide nonwoven fabric or the like to suck up the oxygenated water according to a capillary effect is fixed in the frame.

In more detail, the vessel 44 is provided near the front side (in the cultivating chamber 4) of the outlet 27 as described above, and the frame attached with the absorbing member 56 is erected and fixed in the bottom of the vessel 44. With this configuration, air discharged from the duct 24 through the outlet 27 makes direct contact with the absorbing member 56 and the oxygenated water is evaporated from the absorbing member 56 to properly sterilize the cultivating chamber 4. In addition, the hydrogen peroxide gas concentration in the cultivating chamber 4 is measured using a hydrogen peroxide measuring test paper put in the cultivating chamber 4.

In this manner, in the sterilizing gas generator 42, the absorbing member 56 is dipped into the oxygenated water, and circulating air contacts the absorbing member 56 for a predetermined period of time set by a timer controlled by the controller 60. Thus, the oxygenated water is evaporated and the cultivating chamber 4 is filled with the evaporated oxygenated water. Accordingly, it is possible to effectively generate the sterilizing gas to sterilize the inside of the culture apparatus 1. In particular, since the absorbing member 56 has only to be erected in the vessel 44 filled with the oxygenated water, it is possible to significantly simplify the sterilizing gas generator 42.

Although it has been illustrated in the above embodiments that the sterilizing gas generator 42 is provided within the cultivating chamber 4 of the culture apparatus 1, without being limited to this, the sterilizing gas generator 42 may be provided outside the culture apparatus 1 instead of inside the cultivating chamber 4. In addition, although the hydrogen peroxide has been used as the sterilizer, without being limited to the hydrogen peroxide, the sterilizer may be of any type as long as it can have sterilizing power.

The present invention is not limited to the above-described embodiments but may be effectively changed and modified in various ways without departing from the spirit and scope of the invention.

What is claimed is:

1. A culture apparatus for cultivating cultures in a cultivating chamber, comprising
   a sterilizing gas generator that supplies sterilizing gas into the cultivating chamber;
   an ultraviolet generator that irradiates gas in the cultivating chamber with an ultraviolet ray; and
   a controller that performs a sterilization process for filling the cultivating chamber with the sterilizing gas for a predetermined period of time and a decomposition process for decomposing the sterilizing gas by irradiating the gas in the cultivating chamber with the ultraviolet ray by means of the ultraviolet generator;
   wherein the sterilizing gas generator atomizes a sterilizer solution by means of an ultrasonic vibrator; and wherein the sterilizing gas generator is provided inside the cultivating chamber.

2. The culture apparatus according to claim 1, wherein the sterilizing gas generator evaporates a sterilizer solution by dipping an absorbing member into the sterilizer solution.

3. The culture apparatus according to claim 2, wherein the sterilizing gas concentration in the cultivating chamber is from 0.1 ppm to 100 ppm.

4. The culture apparatus according to claim 1, further comprising
a door for blocking an opening of the cultivating chamber in a free-opening/closing manner and a locking device for prohibiting the door from being opened, wherein the controller controls the locking device to prevent the door from being opened from start of the sterilization process to end of the decomposition process.

5. The culture apparatus according to claim 2, further comprising an ultraviolet generator that irradiates gas in the cultivating chamber with an ultraviolet ray.

6. The culture apparatus according to claim 1, wherein the sterilizing gas concentration in the cultivating chamber is from 0.1 ppm to 100 ppm.

7. The culture apparatus according to claim 6, further comprising an ultraviolet generator that irradiates gas in the cultivating chamber with an ultraviolet ray.

8. The culture apparatus according to claim 7, further comprising
a controller that performs a sterilization process for filling the cultivating chamber with the sterilizing gas for a predetermined period of time and a decomposition process for decomposing the sterilizing gas by irradiating the gas in the cultivating chamber with the ultraviolet ray by means of the ultraviolet generator.

9. The culture apparatus according to claim 8, further comprising
a door for blocking an opening of the cultivating chamber in a free-opening/closing manner and a locking device for prohibiting the door from being opened, wherein the controller controls the locking device to prevent the door from being opened from start of the sterilization process to end of the decomposition process.

10. The culture apparatus according to claim 1, wherein the sterilizing gas concentration in the cultivating chamber is from 0.1 ppm to 100 ppm.

11. The culture apparatus according to claim 10, further comprising an ultraviolet generator that irradiates gas in the cultivating chamber with an ultraviolet ray.

12. The culture apparatus according to claim 11, further comprising
a controller that performs a sterilization process for filling the cultivating chamber with the sterilizing gas for a predetermined period of time and a decomposition process for decomposing the sterilizing gas by irradiating the gas in the cultivating chamber with the ultraviolet ray by means of the ultraviolet generator.

13. The culture apparatus according to claim 12, further comprising
a door for blocking an opening of the cultivating chamber in a free-opening/closing manner and a locking device for prohibiting the door from being opened, wherein the controller controls the locking device to prevent the door from being opened from start of the sterilization process to end of the decomposition process.

14. The culture apparatus according to claim 1, further comprising an ultraviolet generator that irradiates gas in the cultivating chamber with an ultraviolet ray.

15. The culture apparatus according to claim 14, further comprising
a controller that performs a sterilization process for filling the cultivating chamber with the sterilizing gas for a predetermined period of time and a decomposition process for decomposing the sterilizing gas by irradiating the gas in the cultivating chamber with the ultraviolet ray by means of the ultraviolet generator.

16. The culture apparatus according to claim 15, further comprising
a door for blocking an opening of the cultivating chamber in a free-opening/closing manner and a locking device for prohibiting the door from being opened, wherein the controller controls the locking device to prevent the door from being opened from start of the sterilization process to end of the decomposition process.

17. The culture apparatus according to claim 1, further comprising an ultraviolet generator that irradiates gas in the cultivating chamber with an ultraviolet ray.

18. The culture apparatus according to claim 1, wherein the sterilizing gas generator includes the ultrasonic vibrator and a vessel provided in a bottom of an inner box.

* * * * *